US007161016B1

(12) United States Patent  
Makriyannis et al.

(10) Patent No.: US 7,161,016 B1
(45) Date of Patent: Jan. 9, 2007

(54) CANNABIMIMETIC LIPID AMIDES AS USEFUL MEDICATIONS

(75) Inventors: Alexandros Makriyannis, Watertown, MA (US); Atmaram Khanolkar, Storrs, CT (US); Andreas Goutopoulos, Storrs, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 09/600,786

(22) PCT Filed: Nov. 24, 1999

(86) PCT No.: PCT/US99/28136

§ 371 (c)(1),
(2), (4) Date: Jul. 21, 2000

(87) PCT Pub. No.: WO00/32200

PCT Pub. Date: Jun. 8, 2000

Related U.S. Application Data

(60) Provisional application No. 60/109,615, filed on Nov. 24, 1998.

(51) Int. Cl.
*C07C 231/00* (2006.01)
(52) U.S. Cl. .................... 554/67; 554/54; 554/55; 554/61; 564/189; 564/192; 564/193
(58) Field of Classification Search ............... 554/54, 554/55, 61, 67; 564/189, 192, 193
See application file for complete search history.

(56) References Cited

U.S. PATENT DOCUMENTS

| 3,041,343 | A | 6/1962 | Jucker et al. |
|---|---|---|---|
| 3,465,024 | A | 9/1969 | Brownstein et al. |
| 3,573,327 | A | 3/1971 | Miyano |
| 3,577,458 | A | 5/1971 | Brownstein et al. |
| 3,656,906 | A | 4/1972 | Bullock |
| 3,838,131 | A | 9/1974 | Gauthier |
| 3,886,184 | A | 5/1975 | Matsumoto et al. |
| 3,897,306 | A | 7/1975 | Vidic |
| 3,915,996 | A | 10/1975 | Wright |
| 3,928,598 | A | 12/1975 | Archer |
| 3,944,673 | A | 3/1976 | Archer |
| 3,946,029 | A | 3/1976 | Descamps et al. |
| 3,953,603 | A | 4/1976 | Archer |
| 4,036,857 | A | 7/1977 | Razdan et al. |
| 4,054,582 | A | 10/1977 | Blanchard et al. |
| 4,087,545 | A | 5/1978 | Archer et al. |
| 4,087,546 | A | 5/1978 | Archer et al. |
| 4,087,547 | A | 5/1978 | Archer et al. |
| 4,088,777 | A | 5/1978 | Archer et al. |
| 4,102,902 | A | 7/1978 | Archer et al. |
| 4,152,450 | A | 5/1979 | Day et al. |
| 4,171,315 | A | 10/1979 | Ryan |
| 4,176,233 | A | 11/1979 | Archer et al. |
| 4,179,517 | A | 12/1979 | Mechoulam |
| 4,188,495 | A | 2/1980 | Althuis et al. |
| 4,208,351 | A | 6/1980 | Archer et al. |
| 4,278,603 | A | 7/1981 | Thakkar et al. |
| 4,282,248 | A | 8/1981 | Mechoulam et al. |
| 4,382,943 | A | 5/1983 | Winter et al. |
| 4,395,560 | A | 7/1983 | Ryan |
| 4,497,827 | A | 2/1985 | Nelson |
| 4,550,214 | A | 10/1985 | Mehta |
| 4,758,597 | A | 7/1988 | Martin et al. |
| 4,812,457 | A | 3/1989 | Narumiya |
| 4,876,276 | A | 10/1989 | Mechoulam |
| 4,885,295 | A | 12/1989 | Bell et al. |
| 5,053,548 | A | 10/1991 | Tanaka et al. |
| 5,068,234 | A | 11/1991 | D'Ambra et al. |
| 5,147,876 | A | 9/1992 | Mizuchi et al. |
| 5,223,510 | A | 6/1993 | Gubin et al. |
| 5,284,867 | A | 2/1994 | Kloog |
| 5,324,737 | A | 6/1994 | D'Ambra et al. |
| 5,434,295 | A | 7/1995 | Mechoulam et al. |
| 5,440,052 | A | 8/1995 | Makriyannis et al. |
| 5,462,960 | A | 10/1995 | Barth et al. |
| 5,489,580 | A | 2/1996 | Makriyannis et al. |
| 5,521,215 | A | 5/1996 | Mechoulam |
| 5,532,237 | A | 7/1996 | Gallant et al. |
| 5,538,993 | A | 7/1996 | Mechoulam |
| 5,576,436 | A | 11/1996 | McCabe et al. |
| 5,605,906 | A | 2/1997 | Lau |
| 5,607,933 | A | 3/1997 | D'Ambra et al. |
| 5,618,955 | A | 4/1997 | Mechoulam et al. |

(Continued)

FOREIGN PATENT DOCUMENTS

EP 0276732 8/1988

(Continued)

OTHER PUBLICATIONS

Chem. Abstr. 135:137336, abstract of IL-113228, 1999.*

(Continued)

*Primary Examiner*—Deborah D. Carr
(74) *Attorney, Agent, or Firm*—Alix, Yale & Ristas, LLP

(57) ABSTRACT

Novel analogs of arachidonylethanolamide are presented which have higher affinities for the cannabinoid CB1 and/or CB2 receptor sites. Further, most of the analogs exhibit greater metabolic stability than arachidonylethanolamide. The improved receptor affinity and selectivity and/or greater metabolic stability make these analogs therapeutically useful as medications for relief of pain caused by cancer and nausea caused by chemotherapy, as well as for peripheral pain. The compounds may also be useful as oral and topical contraceptives, in suppression of the immune system, enhancement of appetite and in treatment of psychomotor disorders, multiple sclerosis and hypertension.

19 Claims, No Drawings

U.S. PATENT DOCUMENTS

| | | | |
|---|---|---|---|
| 5,624,941 | A | 4/1997 | Barth et al. |
| 5,631,297 | A * | 5/1997 | Pate et al. .................. 514/627 |
| 5,635,530 | A | 6/1997 | Mechoulam |
| 5,688,825 | A | 11/1997 | Makriyannis et al. |
| 5,744,459 | A | 4/1998 | Makriyannis et al. |
| 5,747,524 | A | 5/1998 | Cullinan et al. |
| 5,804,601 | A | 9/1998 | Kato et al. |
| 5,817,651 | A | 10/1998 | D'Ambra et al. |
| 5,872,148 | A | 2/1999 | Makriyannis et al. |
| 5,874,459 | A | 2/1999 | Makriyannis et al. |
| 5,925,628 | A | 7/1999 | Lee et al. |
| 5,925,768 | A | 7/1999 | Barth et al. |
| 5,932,610 | A | 8/1999 | Shohami et al. |
| 5,948,777 | A | 9/1999 | Bender et al. |
| 6,013,648 | A | 1/2000 | Rinaldi et al. |
| 6,028,084 | A | 2/2000 | Barth et al. |
| 6,096,740 | A | 8/2000 | Mechoulam |
| 6,127,399 | A | 10/2000 | Yuan |
| 6,166,066 | A | 12/2000 | Makriyannis et al. |
| 6,284,788 | B1 | 9/2001 | Mittendorf et al. |
| 6,391,909 | B1 | 5/2002 | Makriyannis et al. |
| 6,579,900 | B1 | 6/2003 | Makriyannis et al. |
| 6,610,737 | B1 | 8/2003 | Garzon et al. |
| 2002/0119972 | A1 | 8/2002 | Leftheris et al. |
| 2002/0173528 | A1 | 11/2002 | Fride et al. |
| 2003/0120094 | A1 | 6/2003 | Makriyannis et al. |
| 2003/0149082 | A1 | 8/2003 | Makriyannis et al. |
| 2004/0077649 | A1 | 4/2004 | Makriyannis et al. |
| 2004/0077851 | A1 | 4/2004 | Makriyannis et al. |
| 2004/0087590 | A1 | 5/2004 | Makriyannis et al. |

FOREIGN PATENT DOCUMENTS

| | | |
|---|---|---|
| EP | 0444451 | 9/1991 |
| EP | 0471609 | 6/1993 |
| EP | 0737671 | 10/1996 |
| EP | 0860168 | 9/2001 |
| FR | 2240003 | 5/1975 |
| FR | 2735774 | 1/2000 |
| GB | 2027021 A | 2/1980 |
| JP | 57098228 | 6/1982 |
| JP | 2304080 | 12/1990 |
| WO | WO 94/12466 A | 6/1994 |
| WO | WO 97/00860 | 1/1997 |
| WO | WO 99/57106 | 11/1999 |
| WO | WO 99/57107 | 11/1999 |
| WO | WO 99/64389 | 12/1999 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 02/058636 | 8/2002 |
| WO | WO 02/060447 | 8/2002 |
| WO | WO 03/005960 | 1/2003 |
| WO | WO 03/020217 | 3/2003 |
| WO | WO 03/035005 | 5/2003 |
| WO | WO 03/063758 | 8/2003 |
| WO | WO 03/064359 | 8/2003 |

OTHER PUBLICATIONS

Khanolkar et al., Journal of Med. Chem., vol. 39, pp. 4515-4519, 1996.*

Supplementary European Search Report for EP Application No. 99 96 1838 dated Nov. 1, 2004.

Hanus, L. et al, "Two New Unsaturated Fatty Acid Ethanolamides in Brain That Bind to the Cannabinoid Receptor" Journal of Medicinal Chemistry, vol. 36, No. 20, 1993, pp. 3032-3034.

Mechoulam, R. et al, "Towards cannabinoid drugs—revisited" Progress in Medicinal Chemistry, Elsevier, Amsterdam, NL, vol. 35, Jul. 3, 1998, pp. 199-243.

U.S. Appl. No. 09/698,071, filed Oct. 30, 2000, Fride et al.
U.S. Appl. No. 09/701,989, filed Jun. 9, 1999, Makriyannis et al.
U.S. Appl. No. 10/110,865, filed Oct. 18, 2000, Makriyannis et al.
U.S. Appl. No. 10/110,830, filed Oct. 18, 2000, Makriyannis et al.
U.S. Appl. No. 10/110,812, filed Oct. 18, 2000, Makriyannis et al.
U.S. Appl. No. 10/110,862, filed Oct. 18, 2000, Makriyannis et al.
U.S. Appl. No. 10/111,059, filed Oct. 18, 2000, Makriyannis et al.
U.S. Appl. No. 10/493,093, filed Oct. 28, 2002, Makriyannis et al.
U.S. Appl. No. 10/647,544, filed Aug. 25, 2003, Makriyannis et al.

*1* Abadji V., Lin S., Taha G., Griffin G., Stevenson L.A., Pertwee R.G., Makriyannis A.; "(R)-Methanadamide: a chiral novel anandamide possessing higher potency and metabolic stability"; J. Med. Chem.; 37(12); 1889-1893; 1994; CODEN: JMCMAR; ISSN: 0022-2623; XP002040932.

Alo, B.I.; Kandil, A.; Patil, P. A.; Sharp, M. J.; Siddiqui, M. A.; and Snieckus, V. Sequential Directed Ortho Metalation-Boronic Acid Cross-Coupling Reactions. A general Regiospecific Route to Oxygenerated Dibenzo[b,d]pyran-6-ones Related to Ellagic Acid, J. Org. Chem. 1991, 56, 3763-3768.

***Archer et al; "cannabinoids, synthesis approaches to 9-ketocannabinoids."; J. Org. Chem.; vol. 42; No. 13; 2277-2284; (1977).

Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).

*1* Barnett-Norris et al; "Exploration of biologically relevant conformations of anandamide, . . . "; J. Med. Chem.; vol. 41; 4861-4872; 1998.

Beak, P.; and Brown, R A., The Tertiary Amide as an Effective Director of Ortho Lithiation, J. Org. Chem. 1982, 47, 34-36.

Belgaonkar et al; "synthesius of isocoumarins"; Indian J. Chem; vol. 13; No. 4; 336-338; 1975 (abstract only).

*1* Beltramo M., Stella N., Calignano A., Lin S. Y., Makriyannis A., Piomelli D; "Functional Role Of High-Affinity Anandamide Transport, as Revealed By Selective Inhibition"; Science; vol. 277; 1094-1097; 1997.

*1* Beltramo M., Stella N., Calignano A., Lin S. Y., Makriyannis A., Piomelli D; "Identification and Functional Role of High Affinity Anandamide Transport"; The Neurosciences Institute (1 page).

*1* Beltramo M., Piomelli D; "Anandamide Transport Inhibition by the Vanilloide Agonist Olvanil"; Europeean J. of Pharmacology; (1999); 364(1); 75-78 (abstract only).

Berdyshev EV, Cannabinoid receptors and the regulation of immune response. Chem Phys Lipids. Nov. 2000; 108(1-2):169-90.

*1* Berglund et al; "Structural requirements for arachidonylethanolamide interaction with CB1 and CB2 cannabinoid receptors: . . . "; Prostanglandins, leukotrienes ands essential fatty acids; 59(2); 111-118; (1998). (abstract only).

Bodnar, V.N., Lozinskii, M.O., Pel'kis, P.S.; "Synthesis fo 2,5-disubstituted 1,3,4-oxadiazoles and 1,4-dihydro-1,2,4,5-tetrazine"; Ukrainskii Khimicheskii Zhurnal (Russian Edition); 48(12); 1308-1311; 1982 (abstract only).

Bracey, M et al, Structural Adaptations in a Membrane Enzyme That Terminates Endocannabinoid Signaling. Science 2002; 298(5599): 1793-1796.

Brenneisen R, Pgli A, Elsohly MA, Henn V. Spiess Y: The effect of orally and rectally administered Δ9-tetrahydrocannabinol on spasticity, a pilot study with 2 patients. Int. J. Clin Pharmacol Ther. (1996) 34:446-452. (abstract only).

Brotchie JM: Adjuncts to dopamine replacement a pragmatic approach to reducing the problem of dyskinesia in Parkinson's disease. Mov. Disord. (1998)13:871-876. (abstract only).

Brown et al; "Synthesis and hydroboration of (-)-2-phenylapopinene, Comparison of mono(2-phenylapoisopinocampheyl)borane with its 2-methyl and 2-ethyl analogues for the chiral hydroboration of representative alkenes"; J. Org. Chem.; 55(4); 1217-1223; (1990).

Buckley NE, McCoy KI, Mpzey E et al, "Immunomodulation by cannabinoids is absent in mice deficient for the cannabinoid CB2 receptor"; Eur. J Pharmacol (2000) 396:141-149.

Burstein et al; "detection of cannabinoid receptors . . . "; Biochem. Biophys. Res. Commun.; vol. 176(1); 492-497; 1991 (abstract only).

Busch-Peterson et al; "Unsaturated side chain beta-11-hydroxyhexahydrocannabinol analogs"; J. Med. Chem.; 39; 3790-3796; (1996).

Calignano A, La Rana G. Diuffrida A, Piomelli D; "Control of pain initiation by endogenous cannabinoids"; Nature (1998) 394:277-291, (abstract only).

*1* Calignano A., La Rana G., Beltramo, M., Makriyannis A., Piomelli D; "Potentiation of Anandamide Hypotension by the Transport Zinhibitor, AM404"; Eur. J. Pharmacol.; 1997; 337 R1-R2.

*1* Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7-R8.

Campbell FA et al; "Are cannabinoids an effective and safe treatment option in the management of pain? A qualitative systematic review"; BMJ. Jul. 7, 2001;323(7303):13-6.

Charalambous A. et al; "5'-azido Δ8-THC: A Novel Photoaffinity Label for the Cannabinoid Receptor"; J. Med. Chem., 35, 3076-3079 (1992).

Charalambous A. et al; "Pharmacological evaluation of halogenated . . . "; Pharmacol. Biochem. Behav.; vol. 40; No. 3; 509-512; 1991.

Cheng et al; "Relationship Between the Inhibition Constant (Ki) and the concentration of Inhibitor which causes 50% Inhibition (IC50) of an Enzymatic Reaction"; Biochem. Pharmacol., 22, 3099-3102, (1973) (abstract only).

*1* Cherest M., Luscindi X.; "The action of acetyl chloride and of acetic anhydride on the lithium nitronate salt of 2-phenylnitrioethane . . . "; Tetrahedron; 42(14); 3825-3840; 1986; in French with English abstract.

*1* Cherest M., Lusinchi X.; "A novel electrophilic N-amidation via electron deficient complexes: action of ferric chloride on N-acetyloxyamides"; Tetrahedron Letters; 30(6); 715-718; 1989.

Colombo G, Agabio R, Diaz G. et al; "Appetite suppression and weight loss after the cannabinoid antagonist SR141716"; Life Sci. (1998) 63-PL13-PL117. (abstract only).

*1* Compton D.R. et al; "Pharmacological Profile Of A Series Of Bicyclic Cannabinoid Analogs: Classification as Cannabimimetic Agents"; J. Pharmacol. Exp. Ther.; 260; 201-209; 1992. (abstract only).

Compton et al; "Synthesis and pharmacological evaluation of ether and related analogues of delta8-. delta9 - and delta9,11-tetrahydrocannabinol"; J. Med. Chem; vol. 34; No. 11; 3310-3316; 1991.

Consroe P, Musty R, Rein J, Tillery W, Pertwee R; "The perceived effects of smoked cannabis on patents with multiple sclerosis"; Eur. Neurol. (1997) 38-44-48. (abstract only).

Coxon et al; "Derivatives of nopinone"; Aust. J. Chem.; 23; 1069-1071; (1970) (abstract only).

Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.

D'Ambra et al; "C-attached aminoalkylindoles: potent cannabinoid mimetics"; Bioorg & Med. Chem. Lett., 1996, 6(1), 17-22.

*1* *** D'Amour F.E. et al; "A Method For Determining Loss Of Pain Sensation"; J. Pharmacol. Exp. Ther.; 72; 74-79; 1941.

*1* Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.

DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375-8380.

*1* Desarnaud F., Cadas H., Piomelli D.; "Anandamide amidohydrolase activity in rat brain microsomes"; J. Biol. Chem.; 270; 6030-6035; (1995).

*1* Deutsch D.G. et al; "Fatty acid sulfonyl fluorides inhibit anandamide metabolism and bind to cannabinoid receptor"; Biochem. Biophys. Res. Commun. 231(1); 217-221; 1997; CODEN: BBRCA9; ISSN:0006-291X; XP002040933.

*1* Deutsch D.G., Chin S.A.; "Enzymatic synthesis and degradation of anandamide, a cannabinoid receptor agonist"; Biochemical Pharmacology; 46(5); 791-796; 1993.

Devane, W.A. et al; "Determination and Characterization of a Cannabinoid Receptor in a Rat Brain"; Mol. Pharmacol., 34, 605-613 (1988). (abstract only).

Di Marzo, V., Melck, D., Bisogno, T., DePetrocellis, L.; "Endocannabinoids: endogenous cannabinoid receptor ligands with neuromodulatory action"; Trends Neurosci. (1998) 21:521-528.

*1* Di Marzo, V., Bisogno, T., Melck, D., Ross, R., Brockie, H., Stevenson, L., Pertwee, R., DePetrocellis, L., "Interactions between synthetic vanilloids and the endogenous cannabinoid system"; FEBS Letters; (1998); 437(3); 449-454. (abstract only).

Dodd, P.R. et al, A Rapid Method for Preparing Synaptosomes: Comparison with Alternative Procedures, Brain Res., 226, 107-118 (1981). (abstract only).

Dominiami et al; "Synthesis of 5-(tert-Alkyl)resorcinols"; J. Org. Chem. 42(2); 344-346; (1977).

Drake et al, "classical/nonclassical hybrid cannabinoids"; J. Med. Chem.; vol. 41(19); 3596-3608 (1998).

Edery et al; "Activity of novel aminocannabinoids in baboons"; J. Med. Chem.; 27; 1370-1373 (1984).

Eissenstat et al; "Aminoalkylindoles: structure-activity relationships of novel cannabinoids mimetics"; J. Med. Chem. 1995, vol. 38, No. 16, pp. 3094-3105; XP 000651090.

Fahrenholtz, K. E., Lurie, M. and Kierstead, AR. W.; "The Total Synthesis of dl-Δ9-Tetrahydrocannabinol and Four of Its Isomers"; J. Amer. Chem. Soc. 1967, 89(23), 5934-5941.

Fahrenholtz; "The synthesis of 2 metabolites of (-)-delta eight-tetrahydrocannabinol"; J. Org. Chem.; vol. 37(13); 1972; XP002111824.

Fisera, L., Kovac, J., Lesco, J., Smahovsky, V.; "Furan derivatives. Part CLVI. 1,3-dipolar cycloadditions of heterocycles. V. Reaction of C-acetyl-N-phenylnitrilimine with furan derivatives"; Chemicke Zvesti; 35(1); 93-104 1981 (abstract only).

*1* Fride, E. & Mechoulam, R.; "Pharmacological activity of the cannabinoid receptor agonist, anandamide, a brain constituent"; European Journal of Pharmacology, vol. 231; 313-314; 1993.

Galiegue S et al.; "Expression of central and peripheral cannabinoid receptors in human immune tissues and leukocyte subpopulations"; Eur J Biochem.; Aug. 15, 1995;232(1):54-61. (abstract only).

Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189-194.

Gold et al; "A comparison of the discriminative stimulus properties of detla9-tetrahydrocannabinol and CP 55,940 in rats and rhesus monkeys"; J. Pharmacol. Exp. Ther.; vol. 262(2); 479-486; 1992.

Green K.; "Marijuana smoking vs. cannabinoids for glaucoma therapy."; Arch. Opthamol. (1998) Nov. 116(11); 1433-1437. (abstract only).

Hampson, A.J., Grimaldi M. Axpirod J. Wink D; "Cannabidiol and (-) Δ9 tetrahydrocannabinol are neuroprotective antioxidants"; Proc. Natl Acad Sci. USA (Jul. 1998) 95; 8268-8273.

Hargreaves, K. et al; "A new sensitive method for measuring thermal nociception in cutaneous hyperalgesia"; Pain; 32; 77-88; (1988) (abstract only).

***Hemming M, Yellowlees PM; "Effective treatment of Tourette's syndrome with marijuana"; J. Psychopharmacol, (1993) 7:389-391.

Herzberg U, Eliav E, Bennett GJ, Kopin IJ; "The analgesic effects of R(+) WIN 55,212-2 mesylate, a high affinity cannabinoid agonist in a rat model of neuropathic pain"; Neurosci. Letts. (1997) 221: 157-160.

*1* Hillard C. J., Edgemond, W. S., Jarrahian W., Campbell, W. B.; "Accumulation of N-Arachidonoylethanolamine (Anandamide) into Cerebellar Granule Cells Occurs via Facilitated Diffusion"; Journal of Neurochemistry; 69: 631-638 (1997).

*1* Horrevoets A.J.G et al; "Inactivation of *escherichia coli* outer membrane phospholipase A by the affinity label hexadecanesulfonyl fluoride"; Eur. J. Biochem.; 198; 247-253; 1991.

*1* Horrevoets A.J.G et al; "Inactivation of reconstituted *escherichia coli* outer membrane phospholipase A by membrane-perturbing peptides results in an increased reactivity towards the affinity label hexadecanesulfonyl fluoride"; Eur. J. Biochem.; 198; 255-261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

Howlett et al; "Stereochemical effects of 11-OH-delta 8 tetrahydrocannabinol-dimethylheptyl to inhibit adenylate cyclase and bind to the cannabinoid receptor"; Neuropharmacology; vol. 29(2); 161-165; 1990.

Huffman et al; "3-(1',1'-dimethylbutyl)—deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydrocannabinols"; tetrahedron; vol. 51(4); 1017-1032; (1995).

Huffman et al; "Synthesis of 5',11 dihydroxy delta 8 tetrahydrocannabinol"; Tetrahedron, vol. 53(39), pp. 13295-13306 (1997).

Huffman et al; "Synthesis of a tetracyclic, conformationally constrained analogue of delta 8-THC"; Bioorganic & Medicinal Chemistry; vol. 6(12); 2281-2288; 1998; XP002123230.

Huffman et al; "Synthesis of both enantiomers of Nabilone from a common intermediate. Enantiodivergent synthesis of cannabinoids"; J. Org. Chem.; 1991, 56, 2081-2086.

Joy JE, Wagtson SJ, Benson JA; "Marijuana and Medicine Assessing the Science Base"; National Academy Press, Washington, DC, USA (1999). (abstract only).

Kaminski NE; "Regulation of the cAMP cascade, gene expression and immune function by cannabinoid receptors"; J Neuroimmunol. Mar. 15, 1998;83(1-2):124-32.

*1* Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.

*1* Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515-4519; (1996).

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug. 1998; 19(8):373-81.

*1* Koutek B. et al; "Inhibitors of arachidonyl ethanolamide hydrolysis"; J. Biol. Chem.; 269(37); 22937-40; 1994; CODEN: JBCHA3; ISSN: 0021-9258; XP002040931.

Kumar RN, et al; "Pharmacological actions and therapeutic uses of cannabis and cannabinoids"; Anesthesia, 2001, 56: 1059-1068 (abstract only).

Lan, R et al; "Structure activity relationships of pyrazole derivatives as cannabinoid receptor antagonists"; J. Med. Chem.; vol. 42(4); 769-776; (1999).

*1* Lang, W. et al; "Substrate Specificity and Stereoselectivity of Rat Brain Microsomal Anandamide Amidohydrolase"; J. Med. Chem.; vol. 42(5); 896-902; (1999).

Lavalle et al; "Efficient conversion of (1R, 5R)-(+)-alpha-pinene to (1S, 5R)-(-)-nopinene"; J. Org. Chem.; vol. 51(8); 1362-1365; (1986).

*1* Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

Loev, B., Bender, P. E., Dowalo, F., Macko, E., and Fowler, P.; "Cannabinoids. Structure-Activity Studies Related to 1,2-Dimethylheptyl Derivatives"; J. Med. Chem.; vol. 16(11); 1200-1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

Ludt, R.E. et al; "A comparison of the synthetic utility of n-butyl-lithium and lithium diisopropylamide in the metalations of N,N-dialkyltouamides"; J. Org. Chem.; 38(9); 1668-1674 (1973).

***Maccarron M., *Endocannabinoids and their actions. Vitamins and Hormones 2002*;65:225-255.

*1* Mackie K., Devane W.A., Hille B.; "Anandamide, an endogenous cannabinoid, inhibits calcium currents as a partial agonist in N18 neuroblastoma cells"; Mol. Pharmacol; 44; 498-0503 (1993).

***Markwell, M.A.K., S.M. Haas, L.L. Bieber, and N.E. Tolbert.; "A modification of the Lowry procedure to simplify protein determination in the membrane and lipoprotein samples." 1978; *Anal. Biochem.*87:206-210.

Martin et al; "Behavioral, biochemical, and molecular modeling evaluations of cannabinoid analogs"; Pharmacol. Biochem. Behav.; vol. 40(3); 471-478; 1991.

Martyn CN. Illis LS, Thom J.; "Nabilone in the treatment of multiple sclerosis"; Lancet (1995) vol. 345; pp. 579.

Matsumoto et al; "Cannabinoids 1.1-amino-and 1 mercapto-7,8,9,10-tetrahydro-6h-dibenzo[b,d]pyrans"; J. of Med. Chem.; vol. 20(1); 17-24; 1977; XP00211825.

Maurer M, Henn V, Dittrich A, Hofmann A.; "Delta-9-tetrahydrocannabinol shows antispastic and analgesic effects in a single case double-blind trial."; Eur. Arch. Psychiat. Clin. Neurosci. (1990), 240:1-4. (abstract only).

Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 1996; XP002111823.

*1* Mechoulam et al; Structural Requirements for Binding of Anandamide Type Compounds to the Brain Cannabinoid Receptor; J. Med. Chem.; 1997; 40; 659-667.

Mechoulam et al; "Stereochemical Requirements for cannabinoid activity"; J. Med. Chem.; 23(10); 1068-1072; (1980).

Mechoulam et al; "Synthesis of the individual, pharmacologically distinct, enantiomers of a tetrahydrocannabinol derivative"; Tetrahedron Asymmetry; 1: 311-314; (1990) (abstract only).

***Mechoulam et al; "Synthesis of the individual, pharmacologically distinct, enantiomers of a tetrahydrocannabinol derivative."; *Tetrahedron Asymmetry*; 1:315-318; (1990).

***Mechoulam, "Cannabinoids as therapeutic agents"; *CRC press*, 1986.

*1* Melck, D., Bisogno, T., DePetrocellis, L., Chuang, H., Julius, D., Bifulco, M., DiMarzo, V.; "Unsaturated Long-Chain N-Acyl-vanillyl-amides"; Biochemical and Biophysical Res. Commun.; (1999); 262(1); 275-284. (abstract only).

Meltzer et al; "An improved synthesis of cannabinol and cannabiorcol"; Synthesis; 1981:985 (1981).

Melvin et al; "Structure-Activity Relationships Defining the ACD-Tricyclic Cannabinoids Cannabinoid Receptor Binding and Analgesic Activity"; Drug Design and Discovery; 13(2); 155-166 (1995). (abstract only).

Melvin et al; "Structure-activity relationships for cannabinoid receptor-binding and analgesic activity: studies of bicyclic cannabinoid analogs"; Mol. Pharmacol.; 44(5); 1008-1015 (1993) (abstract only).

Merck Index; 11th edition; "Tetrahydrocannabinols" compound No. 9142; 1989.

***Morgan Dr: Therapeutic Uses of Cannabis. *Harwood Academic Publishers*, Amsterdam. (1997).

***Morris, S,; Mechoulam, R.; and Irene, Y., Halogenation of phenols and Phenyl ethers with Potassium Halides in the Presence of 18-Crown-6 on Oxidation with m-Chloroperbenzoic Acid, *J. Chem. Soc., Perkin Trans.* 1987, 1423-1427.

Muller-Vahl KB, Kolbe H, Schneider U, Emrich, HM Cannabis in movement disorders. Porsch. Kompicmentarmed (1999) 6 (suppl. 3) 23-27. (abstract only).

Muller-Vahl KB, Schneider U, Kolbe H, Emrich, HM.; "Treatment of Tourette's syndrome with delta-9-tetrahydrocannabinol." Am. J. Psychiat.; (1999); 156(3); 495.

\*\*\*Nahas G, Marijuana and Medicine; 1999, *Human Press Inc.*, Totowa, NJ.

\*1\* Neunhoeffer O., Gottschlich R.; "Acylating activity of O-acylated hydroxylamine derivatives"; Justus Liebigs Ann. Chem.; 736; 100-109; 1970; in German with English abstract.

Novak, J et al; Cannabis, part 27, synthesis of 8-, 10- and 11-oxygenated cannabinoids; J. Chem. Soc. Perkin Trans.; 2867-2871; (1983) (abstract only).

Nye et al; "High affinity cannabinoid binding sites in brain membranes labelled with [H]-5'-trimethylammonium delta8-tetrahydrocannabinol"; J. Pharmacol. Exp. Ther.; vol. 234(3); 784-791; 1985.

Pacheco M, et al; "Aminoalkylindoles: Actions On Specific G-Protein-Linked Receptors"; J. Pharmacal. Exp. Ther.; vol. 257, No. 1, pp. 170-183 and 172 Table (1991).

Palmer et al; "Natural and Synthetic Endocannabinoids and Their Structure-Activity Relationships"; Current Pharmaceutical Design; 6; 1381-1397; (2000).

Papahatjis et al; "A new ring-forming methodology for the synthesis of conformationally constrained bioactive molecules"; Chemistry Letters, 192; (2001).

Papahatjis et al; "Pharmacophoric requirements for cannabinoid side chains: multiple bond and C1'-substituted delta8-tetrahydrocannabinols"; J. Med. Chem.; 41(7); 1195-1200; (1998).

Pertwee et al; "AM630, a competitive cannabinoid receptor agonist"; Life Sci. 1995, 56(23/24), 1949-1955; XP 000653566.

Pertwee et al; "Pharmacological characterization of three novel cannabinoid receptor agonists in the mouse isolated vas deferens"; Eur. J. Pharmacol. 1995, 284, 241-247; XP-001041044.

\*1\* Pertwee et al; "Inhibitory effects of certain enantiomeric cannabinoids in the mouse vas deferens and the myenteric plexus preparation of guinea-pig small intestine"; Br. J. Pharmacol.; 105(4); 980-984 (1992). (abstract only).

Pertwee; Pharmacology of cannabinoid CB1 and CB2 receptors; Pharmacol. Ther., vol. 74(2); pp. 129-180; (1997); XP002226467.

Petrov, M.L., Terent'eva, N.A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-Phenylnitrilimine"; Zhurnal Organicheskoi Khimii; 29(7); 1372-1378; (1993) (abstract only).

\*\*\*Pinnegan-Ling D, Musty R.; Marinol and phantom limb pain: a case study. *Proc Inv. Cannabinoid Rea. Sec.* (1994):53.

\*1\* Pinto et al; Cannabinoid Receptor Binding and Agonist Activity of Amides and Esters of Arachidonic Acid; Mol. Pharmacol.; 1994; 46(3); 516-522. (abstract only).

\*1\* Piomelli D., Beltramo M., Glasnapp S., Lin S.Y., Goutopoulos A., Xiw X-Q., Makriyannis A.; "Structural determinants for recognition and translocation by the anandamide transporter"; Proc. Natl. Acad. Sci. USA; 96; 5802-5807; (1999).

Pitt et al; "The synthesis of Deuterium, carbon-14 and carrier free tritium labelled cannabinoids"; Journal of Labelled Compounds; vol. 11(4); 551-575; 1975; XP002123229.

\*1\* Porreca F., Mosberg H.I., Hurst R., Hruby V.J., Burks T.F.; "Roles of mu, delta and kappa opiod receptors in spinal and supraspinal mediation of gastrointestinal transit effects and hot-plate analgesia in the mouse"; J. Pharmacol. Exp. Ther.; 230(2); 341-348; (1994). (abstract only).

Razdan et al; "Drugs derived from cannabinoids. 6. .Synthesis of cyclic analogues of dimethylheptylpyran"; J. Med. Chem.; vol. 19(5); 719-721; 1976 (abstract only).

\*1\* Razdan et al; "Pharmacological and Behavioral Evaluation of Alkylated Anandamide Analogs"; Life Sci.; 1995; 56(23-24); 2041-2048 (abstract only).

Reggio et al; "Characterization of a region of steric interference at the cannabinoid receptor using the active analog approach"; J. Med. Chem. United States; vol. 36(12); 1761-1771; 1993.

Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228-3233.

Rice AS. Cannabinoids and pain. Curr Opin Investig Drugs. Mar. 2001;2(3):399-414. (abstract only).

Richardson JD, Aanonsen I, Hargreaves KM; "Antihyperalgesic effects of a spinal cannabinoids"; Eur. J. Pharmacol. (1998) 346:145-153.

Richardson JD, Kilo S. Hargreaves KM; "Cannabinoids reduce dryperalgesia and inflammation via interaction with peripheral CB1 receptors"; Pain (1998) 75:111-119.

Rinaldi-Carmona et al; "Biochemical and pharmacological characterization of SR141716A, the first potent and selective brain cannabinoid receptor antagonist"; Life Sci.; vol. 56(23/24); 1941-1947 (1995).

Rinaldi-Carmona et al; "SR141716A, a potent and selective antagonist of the brain cannabinoid receptor"; FEBS Lett.; 350; 240-244; (1994).

Rompp Chemie Lexikon; Falbe and Regitz; "band 1-A-C1, 8"; Aufl, Thieme Verlag; Stuttgart, S 569-570; 1989.

Santus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278-87.

\*\*\*Schuel, H., Burkman, L.J., Picone, R.P., Bo, T., Makriyannis, A., Cannabinoid receptors in human sperm. *Mol. Biol. Cell.*, (1997) (8), 325a.

\*1\* Serdarevich B., Caroll K.K., "Synthesis and characterization of 1- and 2-monoglycerides of anteiso fatty acids"; J. Lipid Res.; 7; 277-284; (1966).

Shawali, A.S., Albar, H.A.; "Kinetics and mechanism of dehydrochlorination of N-aryl-C-ethoxycarbonyl formohydrazidoyl chlorides"; Canadian Journal Of Chemistry; 64(5); 871-875; 1986 (abstract only).

Shen M. Thayer SA: Cannabinoid receptor agonists protect cultured rat hippocampal neurons from excitotoxicity. Mol. Pharmacol (1996) 54:459-462.

Shim et al; "Three-dimensional quantitative structure-activity relationship study of the cannabimimetic (aminoalkyl)indoles using comparative molecular field analysis"; J. Med. Chem.; 1998, 41(23); 4521-4532; XP-002212407.

Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.

Simiand J, Keane M, Keane PE, Soubrie P: SR 141716, A CB1 cannabinoid receptor antagonist, selectively reduces sweet food intake in marmoset. Behav. Pharmacol (1998) 9:179-181. (abstract only).

Tetko, I. V. et al; "Volume Learning Algoritm Artificial Neural Networks For 3D QSAR Studies"; J. Med. Chem.; vol. 44, No. 15 (2001) pp. 2411-2420, 2413, 2414 Table 1.

Terranova J-P, Storme J-J Lafon N et al; "Improvement of memory in rodents by the selective CB1 cannabinoid receptor antagonist, SR 141716"; Psycho-pharmacol (1996) 126:165-172 (abstract only).

Tius et al; "Conformationally restricted hybrids of CP-55,940 and HHC: Steroeselective synthesis and activity"; Tetrahedron; 50(9); 2671-2680; (1994) (abstract only).

Ueda, N., Endocannabinoid hydrolases. Prostaglandins & Other Lipid Mediators 2002;68-69:521-534.

\*1\* Vogel Z., Barg J., Levy R., Saya D., Heldman E., Mechoulam R.; "Anandamide, a brain endogenous compound, interacts specifically with cannabinoid receptors and inhibits adenylate cyclase"; J. Neurochem.; 61(1) 352-355; (1993) (abstract only).

Wagner JA, Varga K, Jarai Z, Kunos G; "Mesenteric vasodilation mediated by endothelia anandamide receptors"; Hypertension (1999) 33:429-434.

Watanabe, T.; Muyaura, N.; and Suzuki, A.; "Synthesis of Sterically Hindered Biaryls via the Palladium Catalyzed Cross-Coupling Reaction of Arylboronic Acids or their Esters with Haloarenes"; Synlett 1992, 207-210.

Wiley et al; "Structure activity relationships of indole and pyrrole derived cannabinoids"; J. Pharmacol. Exp. Ther. 1998, 285(3), 995-1004; XP-0017097982.

Wilson et al; "9-nor-delta8-tetrahydrocannabinol, a cannabinoid of metabolic intersts"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydrohexahydrocannabinols. Synthesis, some behavioral and analgesic properties, and comparison with the tetrahydrocannabinols"; J. Med. Chem.; 19(9); 1165-1167; (1976).

Yamada et al; "(Aminoalkyl)indole isothiocyanates as potentiual electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1'-dimethylheptyl)hexahydrocannabinol: a high affinity cannabinoid agonist"; J. Med. Chem.; vol. 37(16); 2619-2622; (1994).

Yan Guo et al; "(−)-11-hydroxy-7'-isothiocyanato-1'-1'dimethylheptyl-delta8-THC: a novel probe for the cannabinoid receptor in the brain"; J. Med. Chem.; 37(23); 3867-3870; (1994).

Lin et al., J. Med. Chem., vol. 41, pp. 5353-5361, 1998.*

\* cited by examiner

CANNABIMIMETIC LIPID AMIDES AS USEFUL MEDICATIONS

This application claims the benefit of Provisional Application No. 60/109,615, filed Nov. 24, 1998.

BACKGROUND OF THE INVENTION

Classical cannabinoids such as the marijuana derived cannabinoid $\Delta^9$-tetrahydrocannabinol, ($\Delta^9$-THC) produce their pharmacological effects through interaction with specific cannabinoid receptors in the body. So far, two cannabinoid receptors have been characterized: CB1 found in the mammalian brain and peripheral tissues and CB2 found only in the peripheral tissues. Compounds which stimulate those receptors have been shown to induce analgesia and sedation, to cause mood elevation including euphoria and dream states, to control nausea and appetite and to lower intraocular pressure. Cannabinoids have also been shown to suppress the immune system and affect the reproductive system. Thus, compounds which stimulate the CB1 and CB2 receptors, directly or indirectly, are potentially useful as oral and topical contraceptive preparations, in treating glaucoma, preventing tissue rejection in organ transplant patients, controlling nausea in patients undergoing chemotherapy, controlling pain and enhancing the appetite in individuals with AIDS Wasting Syndrome.

In addition to acting at the cannabinoid receptors, cannabinoids such as $\Delta^9$-THC also affect cellular membranes, thereby producing undesirable side effects such as drowsiness, impairment of monoamine oxidase function and impairment of non-receptor mediated brain function. The addictive and psychotropic properties of cannabinoids also limit their therapeutic value.

Arachidonylethanolamide (anandamide) is an endogenous lipid that binds to and activates the CB1 cannabinoid receptor with approximately equal affinity to that of $\Delta^9$-THC. Anandamide also exhibits biochemical and pharmacological properties similar to that of $\Delta^9$-THC, albeit with a longer onset time and shorter duration of action. The exact physiological role of anandamide, a cannabinoid agonist, is still not clearly understood. It is known that an enzyme called "anandamide amidase" hydrolyzes anandamide. It is presumed that the magnitude of action and relatively short duration of action of anandamide is due to a rapid inactivation process consisting of carrier-mediated transport into cells followed by intra-cellular hydrolysis by anandamide amidase.

There is considerable interest in developing analogs of anandamide possessing high CB1 receptor affinity and/or metabolic stability. Such analogs may offer a rational therapeutic approach to a variety of disease states, including pain, psychomotor disorders, and multiple sclerosis, in which elevation of anandamide analog levels may bring about a more favorable response with fewer side effects and greater metabolic stability than direct activation of CB1 receptors by anandamide.

SUMMARY OF THE INVENTION

It has now been found that certain novel analogs of anandamide possess improved CB1 receptor affinity and selectivity and/or greater metabolic stability than anandamide. The term "metabolic stability" as used herein refers to the resistance to hydrolysis of the subject anandamide analog by anandamide amidase.

The analogs were prepared by structural modification of anandamide. The modifications were primarily made in the ethanolamido head group and comprised the substitution or addition of alkyl, substituted alkyl, alkenyl and alkynyl groups. Additionally, a number of retro-anandamides, in which the positions of the NH and CO groups are reversed, were prepared. The retro-anandamides comprised the substitution or addition of alkylacetoxy groups. The analogs prepared are summarized in Table 1.

Based on the results of the prepared analogs, it is believed that a number of additional analogs of anandamide and retro-anandamide would provide similar physiological results. These additional analogs comprise the headgroup substitution or addition of alkyl, substituted alkyl, alkenyl, alkynyl and alkylacetoxy groups, as well as cycloalkyl, polycyclic and heterocyclic groups. Further, structural modification may be made to the tail of the anandamide and retro-anandamide analogs, comprising substitution or addition of alkyl, substituted alkyl, O-alkyl, aryl, alkylaryl, O-alkylaryl, cyclic and heterocyclic groups. These analogs are represented in Table 2.

The improved receptor affinity and selectivity and/or metabolic stability create therapeutic uses for the novel analogs. For example, the compounds of the present invention can be effective in the relief of the pain caused by cancer and the nausea resulting from cancer chemotherapy as well as for the relief of peripheral pain. In addition, the compounds disclosed herein may be immunosuppressive and can therefore be used to prevent organ rejection in an individual undergoing an organ transplant. Because the compounds of the present invention enhance the appetite of an individual, they can be used to treat patients with AIDS Wasting Syndrome, who are often suffering from malnourishment as a result of appetite loss. The compounds could also be used to treat psychomotor disorders, multiple sclerosis, peripheral hypertension and as oral and topical contraceptives.

DESCRIPTION OF SOME PREFERRED EMBODIMENTS

The known physiological activity of cannabinoids, such as $\Delta^9$-THC, and endogenous lipids, such as anandamide, indicate that other novel lipid materials may also interact with the specific cannabinoid receptors. Further, the novel lipid materials can be more resistant to hydrolysis by anandamide amidase than is anandamide, providing a greater magnitude of action and longer duration of action than anandamide. Additionally, the novel lipid materials can have high r affinities for specific cannabinoid receptors than anandamide. Specific analogs of anandamide and retro-anandamide were prepared and tested according to the procedures and protocols discussed below.

Typical procedures for synthesizing the novel analogs of anandamide are as follows:

3(1'R)-1'-Methyl-2'-hydroxyethly)-4,5-diphenyloxazolidin-2-one. A solution of 1.16 g (15.4 mmol) of R-alaninol in 12 mL of anhydrous dimethylformamide was cooled in an ice-bath. 4,5-Diphenyl-1,3-dioxol-2-one 3.67 g (15.4 mmol) was added in one portion and the resulting solution was stirred at room temperature for 1.5 hours. At the end of time period, the reaction mixture was diluted with 50 mL of water and extracted with ethyl acetate (75 mL, 50 mL). Combined organic extracts were dried (MgSO$_4$) and evaporated to afford a colorless oil to which 7 mL of anhydrous trifluoroacetic acid was added and the resulting solution was allowed to stand at room temperature for 2 hours. Methylene chloride was added to the reaction mixture which was found to be a mixture of the title product and the corresponding trifluoroacetate ester. The solution was washed with water, 10% sodium bicarbonate, water and dried (MgSO$_4$). Rotary evaporation of the solvent gave an oil which was dissolved in 15 mL of 95% methanol, 1.5 g of potassium carbonate was added and the heterogenous mixture was stirred for 5 min at room temperature. After dilution with water, the mixture was extracted with methylene chloride, combined organic extracts were dried (MgSO$_4$) and evaporated. The residue was purified by column chromatography on silica gel (80% ethyl-petroleum ether) to afford a white solid (4.0 g, 92%); m.p. 126–128° C., Optical rotation +23.6 (16.4, CHCl$_3$). $^{13}$C NMR (CDCl$_3$), δ 130.9, 130.3, 129.6, 128.4, 127.7, 124.3, 64.0, 52.4, 14.7.

3((1'R)-1' Methyl-2'-fluoroethyl)-4,5 diphenyloxazolidin-2-one.

A solution of 1.08 mL (8.14 mmol) of diethylaminosulfur trifluoride (DAST) in 40 mL of anhydrous methylene chloride was cooled to −78° C. and a solution of 2.0 g (6.78 mmol) of "ox" protected R-alaninol was added dropwise over 5–10 min. The cooling bath was removed and the reaction mixture was stirred at room temperature for 5 hours. Reaction was quenched by addition of 5 mL of water, organic layer was separated, dried (MgSO$_4$) and evaporated. The residue was purified by column chromatography on silica gel (50% ethyl ether-petroleum ether) to afford 0.9 g (74%) of white solid. m.p. 127–129° C., Optical rotation −6.56° (15.3, CHCl$_3$), $^{13}$C NMR (CDCl$_3$) δ 131.1, 130.4, 129.7, 128.5, 127.7, 124.4, 82.2 (d, J CF=172.7 Hz), 50.2 (d, J$_{CF}$=19.8 Hz, 13.4 (d, J$_{CF}$=6.5 Hz).

Analog 1, N-(2-Fluoro-1R-(methylethyl) arachidonylamide). 3(1'R)—I'-Methyl-2'-fluoroethyl) 4,5-diphenyloxazolidim 2-one (100 mg, 0.34 mmol) was dissolved in 14 mL of absolute ethanol. Palladium on charcoal (10%) 57 mg was added and the solution was hydrogenated at 45 psi for 30 hours. After acidification with conc. HCl, solution was filtered through celite. The filtrate was concentrated to afford the HCl salt of (2R)-1-fluoro-2-propylamine, which was coupled with arachidonic acid chloride as described below.

In another flask, a solution of 100 mg (0.33 mmol) of arachidonic acid and 0.06 mL of dry dimethylformamide in 2 mL of dry methylene chloride was cooled in an ice-bath. Then a 2 M solution of oxalyl chloride in methylene chloride (0.33 mL, 2 equiv) was added dropwise. Reaction mixture was stirred at ice-bath temperature under argon for 1 hour. The above (2R)-1-fluoro-2-propylamine as a solution in 0.5 mL of pyridine was added and the reaction mixture was stirred at room temperature for 30 min. The solution was transferred to a separatory funnel and washed with 10% hydrochloric acid, water, and dried. After rotary evaporation, the residue was purified by column chromatography on silica gel (50% ethyl ether-petroleum ether) as eluent to afford colorless oil: [α]+10.82 (4.62, CHCl$_3$).

Analog 2, N-(2-Fluoro-IS-(methylethyl) arachidonylamide, was prepared using the same procedure from N-t-BOC-S-alaninol.

Tosylate of (N-t-BOC—R-Alaninol). A solution of N-t-BOC—R-alaninol (1.4 g, 7.99 mmol) and 1.95 mL (24 mmol) of dry pyridine in 7 mL of dry chloroform was cooled in an ice-bath and a solution of p-toluenesulfonylchloride (2.67 g, 16 mmol) in 3 mL of dry chloroform was added portionwise over a period of 3 hours. The reaction mixture was stirred at ice-bath temperature for 2 hours and then transferred to a separatory funnel with more chloroform and washed successively with 10% hydrochloric acid, 10% sodium bicarbonate and water and dried (MgSO$_4$). Solvent was removed and the residue was purified by column chromatography on silica gel to afford 2.20 g (84%) of viscous colorless oil. 3-Azido-2-(N-t-BOC-amino) propane. Sodium azide (3.62 g, 56 mmol) was added to a solution of the above tosylate (1.0 g, 3.04 mmol) and the heterogenous mixture was heated in an oil-bath at 60–70° C., with stirring, for 2 hours [CAUTION: Use a safety shield]. The reaction mixture was cooled to room temperature, poured into water and extracted with diethyl ether. Combined ether extracts were dried (MgSO$_4$) and ether evaporated. The residue was purified by column chromatography to afford 354 mg (58%) of a colorless oil.

Analog 4, (R)-(+−)-Arachidonyl-1'-azido-2'-propylamide. The above azide was cooled in an ice-bath and 3 mL of dry trifluoroacetic acid was added. The flask was stoppered and the light yellow solution was stirred at room temperature for 2 hours. Most of the trifluoroacetic acid was removed in vacuo. In another flask, arachidonic acid chloride was prepared from 100 mg (0.33 mmol) of arachidonic acid as described in our previous publication. A solution of 1.5 mL of anhydrous pyridine was added at 0° C. The reaction mixture was stirred at room temperature for 30 min and then transferred into a separatory funnel using additional dichloromethane. The solution was washed successively with 10% hydrochloric acid, water, dried (MgSO$_4$) and solvents removed. The residue was purified by column chromatography (30–40% diethyl ether-petroleum ether) to give (82%) of analog 4.

Analog 5, N-(2-Chloroethyl)arachidonylamide. A solution of arachidonic acid (50 mg, 0.165 mmol) and 0.03 mL of anhydrous DMF in 1 mL of dry dichloromethane was cooled in an ice bath under argon and 0.17 mL of a 2 M solution of oxalyl chloride (0.34 mmol) in dichloromethane was added dropwise. Reaction mixture was stirred further at ice bath temperature for 1 hour. A solution of 65 mg (0.50 mmol, 3 equiv) of 2-chloroethylamine hydrochloride in 0.5 mL of dry pyridine was added, the cooling bath was removed, and the solution was stirred at room temperature for 30 min. The mixture was transferred to a separatory funnel, washed with 10% aqueous hydrochloric acid and water, and dried (MgSO$_4$). After rotary evaporation of solvents, the residue was chromatographed on silica gel (60% ethyl ether-petroleum ether) to afford 54 mg (90%) of the pure title compound as an oil: R$_f$ (70% ethyl ether-petroleum ether) 0.35; $^1$H NMR (270 MH$_Z$, CDCl$_3$) 5.80 (br s, 1H), 5.36 (m, 8H), 3.61 (m, 4H), 2.80 (m, 6H), 2.21 (t, J=7.89 Hz, 2H), 2.10 (m, 4H), 1.72 (m, 2H), 1.29 (m, 6H), 0.88 (t, J=6.79 Hz, 3H). Anal. (C$_{22}$H$_{36}$CINO) C, H, N.

Analog 6, N-(3-Chloropropyl)arachidonylamide. The title amide was prepared from 50 mg (0.165 mol) of arachidonic acid as described for analog 5: yield 55 mg (88%); R$_f$ (70% ethyl ether-petroleum ether) 0.35; $^1$H NMR (270 MH$_Z$, CDCl$_3$) 5.60 (br s, 1H), 5.36 (m, 8H), 3.57 (t, J=6.40 Hz, 2H), 3.40 (q, J=6.45 Hz, 2h), 2.80 (m, 6H), 2.18 (t, J=7.91 Hz, 2H), 2.01 (m, 6H), 1.70 (m, 2H), 1.29 (m, 6H), 0.88 (t, J=6.89 Hz, 3H). Anal. (C$_{22}$H$_{38}$CINO) C, H, N.

Analog 7, N-Allylarachidonylamide. Arachidonic acid chloride was prepared from 50 mg (0.165 mmol) of arachidonic acid as described under analog 5 and treated with 0.061 mL (0.83 mmol, 5 equiv) of allylamine. Similar work up followed by column chromatographic purification gave 48 mg (85%) of the pure title compound as an oil: R$_f$ (40% ethyl ether-petroleum ether) 0.18; $^1$H NMR (270 MH$_Z$, CDCl$_3$) 5.83 (m, 1H), 5.36 (m, 9H), 5.14 (m, 2H), 3.87 (m, 2H), 2.80 (m, 6H), 2.19 (t, J=7.93 Hz, 2H), 2.10 (m, 4H), 1.72 (m, 2H), 1.29 (m, 6H), 0.88 (t, J=6.74 Hz, 3H). Anal. (C$_{23}$H$_{37}$N$_O$) C, H, N.

Analog 8, N-Propargylarachidonylamide. Arachidonic acid chloride was prepared from 50 mg (0.165 mmol) of arachidonic acid as described above for analog 5 and treated with 0.057 mL (0.83 mmol, 5 equiv) of propargylamine. Similar work up followed by column chromatographic purification gave 47.8 mg (85%) of the pure title compound as an oil: R$_f$ (70% ethyl ether-petroleum ether) 0.30; H$^1$ NMR (270 MHZ, CDCl$_3$) 5.57 (br s, 1H), 5.36 (m, 8H), 4.04 (m, 2H), 2.80 (m, 6H), 2.22-2.00 (m, 7H), 2.01 (m, 6H), 1.72 (m, 2H), 1.29 (m, 6H), 0.88 (t, J=6.73 Hz, 3H). Anal. (C$_{23}$H$_{35}$NO) C, H, N.

Analog 9, N-(2,2,2-Trifluroethyl) arachidonylamide. Arachidonic acid chloride was prepared from 50 mg (0.165 mmol) of arachidonic acid as described under analog 5 and reacted with a solution of 111.8 mg (0.825 mmol, 5 equiv) of 2,2,2-trifluoroethylamine hydrochloride in 0.5 mL of pyridine. Reaction mixture was stirred at room temperature for 30 min and worked up in a similar manner to give 47.4 mg (75%) of the title amide: $R_f$ (35% ethyl ether-petroleum ether) 0.20; $^1$H NMR (270) MHZ, CDCl$_3$) 5.60 (br s, 1H), 5.36 (m, 8H), 3.91 (m, 2H), 2.80 (m, 6H), 2.24 (t, J=7.39 Hz, 2H), 2.08 (m, 6H), 2.01 (m, 6H), 1.74 (m, 2H), 1.29 (m, 6H), 0.88 (t, J=6.56 Hz, 3H). Anal. (C$_{22}$H$_{34}$F$_3$NO) C, H, N.

Arachidonyl alcohol: To a magnetically stirred solution of 0.5 ml (0.5 mmol) of LiAlH$_4$ in Et$_2$O, 100 mg (0.314 mmol) of arachidonic acid methyl ester in 2 mL of Et$_2$O was added dropwise at 0° C. The reaction mixture was stirred for 1 h and then quenched by addition of 1 mL of EtOAC. 2 mL of saturated NH$_4$Cl solution was added and the organic layer was separated, dried with MgSO$_4$, filtered and evaporated. Chromatography on silica gel (eluents: CH$_2$Cl$_2$/petroleum ether up to 70% CH$_2$Cl$_2$), evaporation, followed by membrane filtration of a CH$_2$Cl$_2$ solution of the product gave 99.3 mg (0.292 mmol, 93% yield) of arachidonyl alcohol as a colorless oil: TLC (CHCl$_3$) $R_f$ 0.28; $^1$H NMR (200 MHZ, CDCl$_3$) δ 5.37 (m, 8 H), 3.61 (t, 2 H, J=6 Hz), 2.79 (m, 6H), 2.08 (m, 4 H), 1.66–1.17 (m, 8H), 0.92 (t, 3H, J=7 Hz); Anal. C, H.

Arachidonylamine. To a magnetically stirred solution of 50 mg (0.17 mmol) of arachidonyl alcohol in 1 mL of pyridine was added 29.2 mg (0.225 mmol) of mesyl chloride at 0° C. After stirring for 5 hours, the reaction mixture was poured into 2 mL of cold water and extracted with diethyl ether (2×4 mL). The combined ether extracts were washed with 1 N sulfuric acid and saturated sodium bicarbonate solution and evaporated in vacuo. The crude mesylate was dissolved in 2 mL of anhydrous DMF, and then a solution of 6.5 mg (0.85 mmol) of sodium azide in 4 mL of anhydrous DMF was added at room temperature. The reaction mixture was heated to 90° C. for 24 hours behind a safety shield. The mixture was cooled to room temperature, inorganic material was filtered off, and the filtrate was poured into 1 mL of cold water. Extraction with diethyl ether (2×6 mL), drying (MgSO$_4$), and evaporation gave an oily residue which was chromatographed on silica gel (petroleum ether) to afford 39 mg (73%) of arachidonyl azide as a colorless oil: $^1$H NMR (200 MHZ, CDCl$_3$) δ 5.38 (m, 8H), 3.27 (t, J=6 Hz, 2H), 2.81 (m, 6H), 2.11–2.01 (m, 4H), 1.62 (m, 2H), 1.48–1.25 (m, 6H), 0.89 (t, J=7 Hz, 3H).

The crude azide was reduced to the title amine as follows: To a magnetically stirred solution of 132 mg (0.43 mmol) of arachidonyl azide in 3 mL of dry diethyl ether was added 4 mL of 1.0 M solution of lithium aluminum hydride (4.0 mmol) in THF dropwise at room temperature. The reaction mixture was refluxed for 3 hours and then quenched with wet diethyl ether. The white suspension was filtered, and the filtrate was evaporated to dryness. Chromatography on silica gel (10–50% MeOH in dichloromethane) gave 65 mg (51%) of arachidonylamine as a white solid: TLC (20% EtOAc—CH2Cl2) $R_f$ 0.33; $^1$H NMR (200 MHZ, CDCl$_3$) δ5.38 (m, 8H), 2.82 (m, 6H), 2.70 (t, J=6.6 Hz, 2H), 2.08 (m, 4H), 1.40 (m, 4H), 1.26 (m, 6H), 0.89 (t, J=6.4 Hz, 3H). Anal. (C$_{20}$H$_{35}$N)C, H, N.

Analog 10, N-(3-Hydroxypropionyl)arachidonylamine. To a magnetically stirred solution of 48 mg (0.17 mmol) of arachidonylamine in 2 mL of anhydrous dichloromethane was added 58 μL of a 2.0 M solution of trimethylaluminum (0.17 mmol) in hexane at room temperature. The mixture was stirred for 20 min, and then 12.24 mg (0.17 mmol) of β-propiolactone was added. The reaction mixture was refluxed for 6 hours, quenched with 1 N HCl, and extracted with dichloromethane. The crude product was purified by column chromatography on silica gel (50–80% ethyl acetate in dichloromethane) to afford 51 mg (83%) of the title compound as an oil: TLC (EtOAc) $R_f$ 0.26; $^1$H NMR (200 MHZ, CDCl$_3$) δ 5.35 (m, 8H), 3.85 (q, J=5.4 Hz, 2H), 3.25 (q, J=5.4 Hz, 2H), 2.84 (m, 6H), 2.66 (t, J=6.8 Hz, 2H), 2.05 (m, 4H), 1.57 (m, 2H), 1.35 (m, 6H) 0.89 (t, J=6.5 Hz, 3H). Anal. (C$_{23}$H$_{39}$NO$_2$) C, H, N.

Analog 11, N-(2-Acetoxyacetyl)arachidonylamine. To a magnetically stirred solution of 75 mg (0.26 mmol) of arachidonylamine in 2 mL of dry dichloromethane was added 40 μL (0.37 mmol) of acetoxyacetyl chloride at room temperature, and the mixture was stirred for 1 h. Excess acetoxyacetyl chloride was destroyed by adding 50 μL of water, solvents were evaporated, and the residue was chromatographed on silica gel (10–25% ethyl acetate in CH$_2$Cl$_2$) to afford 71 mg (70.2%) of the title amide as an oil: $R_f$ (EtOAc) 0.79; $^1$H NMR (200 MHZ, CDCl$_3$) δ 5.37 (m, 8H), 4.55 (s, 3H), 3.32 (q, J=7 Hz, 2H), 2.81 (m, 6H), 2.18 (s, 3H), 2.09 (m, 4H), 1.50-1.25, (m, 6H), 0.92 (t, J=7 Hz, 3H). Anal. (C$_{24}$H$_{39}$NO$_3$) C, H, N.

Certain prepared anandamide analogs were assayed for cannabinoid receptor affinity following the protocol of Example 1. The test results are summarized in Table 1. As used herein, AA refers to a portion of the anandamide molecule having the structure:

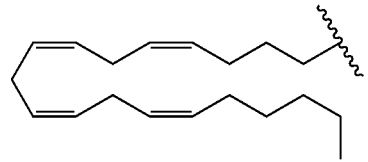

EXAMPLE 1

It is known that the enzymatic action of anandamide amidase can be moderated or prevented in vitro by the inclusion of phenylmethanesulfonyl fluoride (PMSF). PMSF functions as a nonselective protease inhibitor. Thus the ligand binding determinations for the CB1 receptor were carried out in the presence and absence of PMSF, to obtain both CB1 receptor binding affinity and a relative measure of the analog's metabolic stability. The binding affinities ($K_i$) are expressed in nanomoles (nM).

For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107–118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605–613 (1988) and A. Charalambous et al, 5'-*azido* Δ$^8$-*THC: A Novel Photoaffinity Label for the Cannabinoid Receptor*, J. Med. Chem., 35, 3076–3079 (1992) with the following changes. The above articles are incorporated by reference herein.

Membranes, previously frozen at −80° C., were thawed on ice. To the stirred suspension was added three volumes of 25 mM Tris-HCl buffer, 5 mM MgCl$_2$ and 1 mM EDTA, pH 7.4 (TME) containing 150 μM PMSF (made fresh in 2-propanol as a 100 mM stock). The suspension was incubated at 4° C., and after 15 min a second addition of PMSF stock brought the concentration to 300 μM PMSF; then the mixture was incubated for another 15 min. At the end of the second 15-min incubation, the membranes were pelleted and washed three times with TME to remove un-reacted PMSF.

The treated membranes Were subsequently used in the binding assay described below. Approximately 30 μg of PMSF-treated membranes were incubated in silanized 96-well microtiter plate with TME containing 0.1% essentially fatty acid-free bovine serum albumin (BSA), 0.8 nM [$^3$H] CP-55,940, and various concentrations of anandamide analogues in a final volume of 200° C. for 1 hour. The samples were filtered using Packard Filtermate 196 and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the using the assumptions of Cheng et al, *Relationship Between the Inhibition Constant ($K_i$) and the concentration of Inhibitor which causes 50% Inhibition ($IC_{50}$) of an Enzymatic Reaction*, Biochem. Pharmacol., 22, 3099–3102, (1973), which is incorporated by reference herein.

The CB1 ligand binding determinations in the absence of PMSF were performed in a similar manner to the above test, except without the use of PMSF.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107–118 (1981). Silanized centrifuge tubes were used throughout to minimize receptor loss due to adsorption. The CB2 binding assay was conducted in the same manner as for the CB1 binding assay except the assays were conducted without PMSF. Since the CB2 receptor preparation has been shown to be devoid of anandamide amidase, the presence or absence of PMSF was not considered to be determinative. The binding affinities ($K_i$) are expressed in nanomoles (nM). The test results are summarized in Table 1.

TABLE 1

Anandamide Analog Cannabinoid Receptor Site Binding Affinities

| Analog | $K_I$ (CB1), nM | | $K_I$ (CB2), nM |
|---|---|---|---|
| | with PMSF | without PMSF | |
| 1 | 1.18 | 10.1 | 785 |
| 2 | 0.91 | 56.3 | 1336 |
| 3 | 19.1 | 19.5 | 1394 |
| 4 | 12.7 | 25.6 | 1228 |
| 5 | 5.29 | 3400 | 195 |
| 6 | 25.6 | 387 | 193 |
| 7 | 9.91 | 2980 | 226 |
| 8 | 10.8 | 4900 | 290 |
| 9 | 36.2 | 2380 | 718 |
| 10 | 115 | 134 | 3540 |
| 11 | 421 | 419 | >10000 |
| 12 | 20 | 23 | — |

With reference to Sonyuan LIN et al, *Novel Analogues of Arachidonylethanolamide (Anandamide): Affinities for the CB1 and CB2. Cannabinoid Receptors and Metabolic Stability*, Journal of Medicinal Chemistry, Vol 41, No 27, 5353–5361, (1998), which article is incorporated by reference herein, anandamide has been found to have a CB1 $K_i$ of 61.0 nM (with PMSF); a CB1 $K_i$ of 5810 nM (without PMSF); and a CB2 $K_i$ of 1930 nM. As can be seen from Table 1, virtually all of the analogues have higher affinities to the CB1 and CB2 receptor sites than does anandamide. Further, most of the analogues exhibit much smaller differences for the CB1 affinities with and without PMSF, indicating greater metabolic stability than anandamide.

Retro-anandamides are defined as anandamide analogs in which the position of the NH and CO groups have been reversed. Analogs 10, 11 and 12 are examples of some retro-anandamides. It should be noted that the retro-anandamides as a group show excellent affinity to, and selectivity for, the CB1 receptor. Further, the retro-anandamides show virtually no difference in CB1 affinities when tested with and without PMSF. Thus the retro-anandamides exhibit excellent metabolic stability.

The results demonstrate that the retro-anandamides are not substrates for anandamide amidase and therefore are not susceptible to its hydrolytic actions.

PROPHETIC EXAMPLE 2

Based on the above testing and results, it is believed that lipid compounds based on structural formulas 1 and 2, illustrated in Table 2, would exhibit increased cannabinoid receptor affinities and/or selectivities as well as increased metabolic stability. In fact, structural formulas 1 and 2 include analogs 1-12 discussed above.

TABLE 2

Structural Formula 1:

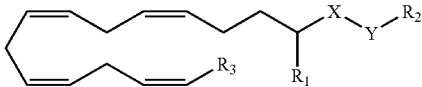

X is one of the group consisting of C=O and NH and Y is the other of that group. Expressed another way, X may be C=O and Y may be NH, or Y may be C=O and X may be NH, but both X and Y may not be the same group.

$R_1$ is selected from the group consisting of H and alkyl groups. More specifically, $R_1$ is selected from the group consisting of H, $CH_3$ and $(CH_3)_2$.

$R_2$ is selected from the group consisting of alkyl, substituted alkyl, alkenyl and alkynyl groups. More specifically, $R_2$ is selected from the group consisting of $CH(R)CH_2Z$, $CH_2CH(R)Z$ and $CH(R)(CH_2)nCH_2Z$, R being selected from the group consisting of H, CH, $CH_3$, CHCH, $CH_2CF_3$ and $(CH_3)_2$, Z being selected from the group consisting of H, halogens, $N_3$, NCS and OH and n being selected from the group consisting of 0, 1 and 2.

$R_3$ is selected from the group consisting of alkyl, substituted alkyl, aryl, alkylaryl, O-alkyl, O-alkylaryl, cyclic and heterocyclic groups. As used herein, O-alkyl and O-alkylaryl refer to groups in which an oxygen atom is interposed between carbon atoms on the anandamide portion and substituent group. Non-limiting examples of such $R_3$ groups include cyclohexyl, cyclopentyl, alkylcyclohexyl, alkylcyclopentyl, piperidinyl, morpholinyl and pyridinyl. More specifically, $R_3$ is selected from the group consisting of n-$C_5H_{10}Z'$, n-$C_6H_{12}Z'$, n-$C_7H_{14}Z'$ and 1',1'-$C(CH_3)_2(CH_2)_5CH_2Z'$, Z' being selected from the group consisting of H, halogens, CN, $N_3$, NCS and OH.

Structural Formula 2:

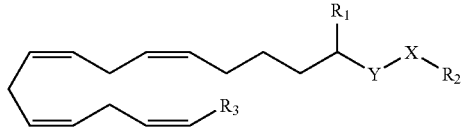

Y is one of the group consisting of C=O and NH and X is the other of that group.

$R_1$ is selected from the group consisting of H and alkyl groups. More specifically, $R_1$ is selected from the group consisting of H, $CH_3$ and $(CH_3)_2$.

$R_2$ is selected from the group consisting of alkyl, substituted alkyl, alkenyl, alkynyl, O-alkyl, cyclic, polycyclic and heterocyclic groups.

More specifically, $R_2$ is selected from the group consisting of

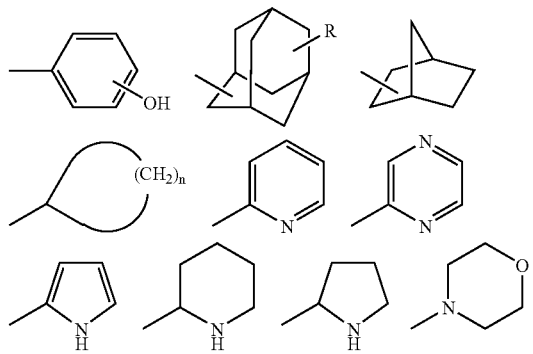

$CH=CH_2$, $CH=C(CH_3)_2$, $C\equiv CH$, $CH_2OCH_3$, $CH(R)(CH_2)nCH_2Z$ and $CH_2CH(R)(CH_2)nZ$, R being selected from the group consisting of H, $CH_3$ and $(CH_3)_2$, Z being selected from the group consisting of H, halogens, $N_3$, NCS, OH and OAc and n being selected from the group consisting of 0, 1 and 2; and $R_3$ is selected from the group consisting of alkyl, substituted alkyl, aryl, alkylaryl, O-alkyl, O-alkylaryl, cyclic and heterocyclic groups. Non-limiting examples of such $R_3$ groups include cyclohexyl, cyclopentyl, alkylcyclohexyl, alkylcyclopentyl, piperidinyl, morpholinyl and pyridinyl. More specifically, $R_3$ may be selected from the group consisting of n-$C_5H_{10}Z'$, n-$C_6H_{12}Z'$, n-$C_7H_{14}Z'$ and 1',1'-$C(CH_3)_2(CH_2)_5CH_2Z'$, Z' being selected from the group consisting of H, halogens, CN, $N_3$, NCS and OH.

Those skilled in the art will recognize, or be able to ascertain with no more than routine experimentation, many equivalents to the specific embodiments of the invention disclosed herein. Such equivalents are intended to be encompassed by the scope of the invention.

What is claimed is:
1. A compound of the formula:

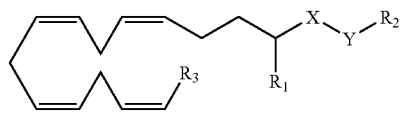

wherein X is one of the group consisting of C=O and NH and Y is the other of that group;

$R_1$ is selected from the group consisting of H, $CH_3$ and alkyl;

$R_2$ is selected from the group consisting of alkyl, substituted alkyl, alkenyl, alkynyl, O-alkyl, cycloalkyl, polycyclic, heterocyclic, $CH_2CH=CH_2$, $C\equiv CH$, $CH(R)CH_2Z$, $CH_2CH(R)Z$ and $CH(R)(CH_2)nCH_2Z$, R being selected from the group consisting of H, $CH_3$, $CH_2CF_3$ and $(CH_3)_2$, Z being selected from the group consisting of H, halogens, N$_3$, NCS and OH and n being selected from the group consisting of 0, 1 and 2; and R$_3$ is selected from the group consisting of alkyl, substituted alkyl, aryl, alkylaryl, O-alkyl, O-alkylaryl, cyclic radical, heterocyclic radical, n-C$_5$H$_{10}$Z', n-C$_6$H$_{12}$Z', n-C$_7$H$_{14}$Z' and 1',1'-C(CH$_3$)$_2$(CH$_2$)$_5$CH$_2$Z', Z' being selected from the group consisting of H, halogens, CN, N$_3$, NCS and OH;

with the proviso that:

when X is C=O, Y is NH, R$_1$ is H, R$_3$ is n-C$_5$H$_{10}$Z' and Z' is H, then R$_2$ can not be selected from the group consisting of C$_{1-5}$ alkyl, CH$_2$CH$_2$OH, CH(CH$_3$)CH$_2$OH, (CH$_2$)$_m$OH (where m=1–10), CH(CH$_3$)CH$_2$F and CH$_2$CH$_2$OMe; and when X is C=O, Y is NH, R$_1$ is H, R$_3$ is selected from n-C$_6$H$_{12}$Z', n-C$_7$H$_{14}$Z', and 1'1'-C(CH$_3$)$_2$(CH$_2$)$_5$CH$_2$Z' and Z' is H, then R$_2$ cannot be selected from the group consisting of C$_{1-5}$ alkyl and (CH$_2$)$_m$OH (where m=1–10).

2. The compound of claim 1 wherein X is NH, Y is C=O, R$_1$=H, R$_2$=CH(R)CH$_2$Z, R=CH$_3$ and Z=F, and R$_3$=n-C$_5$H$_{10}$Z', Z'=H.

3. The compound of claim 1 wherein X is NH, Y is C=O, R$_1$=H, R$_2$=CH(R)CH$_2$Z, R=CH$_3$ and Z=I, and R$_3$=n-C$_5$H$_{10}$Z', Z'=H.

4. The compound of claim 1 wherein R$_1$=H, R$_2$=CH(R)CH$_2$Z, R=CH$_3$ and Z=N$_3$, and R$_3$=n-C$_5$H$_{10}$Z', Z'=H.

5. The compound of claim 1 wherein X is NH, Y is C=O, R$_1$=H, R$_2$=CH(R)CH$_2$Z, R=H and Z=Cl, and R$_3$=n-C$_5$H$_{10}$Z', Z'=H.

6. The compound of claim 1 wherein X is NH, Y is C=O, R$_1$=H, R$_2$=CH(R)(CH$_2$)nCH$_2$Z, R=H and n=1 and Z=Cl, and R$_3$=n-C$_5$H$_{10}$Z', Z'=H.

7. The compound of claim 1 wherein R$_1$=H, R$_2$=CH$_2$CH(R)Z, R=CH$_3$ and Z=Cl, and R$_3$=n-C$_5$H$_{10}$Z', Z'=H.

8. The compound of claim 1 wherein R$_1$=H, R$_2$=CH$_2$CH=CH$_2$ or C≡CH, and R$_3$=n-C$_5$H$_{10}$Z', Z'=H.

9. The compound of claim 1 wherein R$_1$=H, R$_2$=CH$_2$CF$_3$, and R$_3$=n-C$_5$H$_{10}$Z', Z'=H.

10. A compound of the formula:

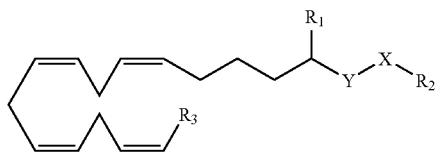

wherein X is one of the group consisting of C=O and NH and Y is the other of that group;

R$_1$ is selected from the group consisting of H, CH$_3$ and alkyl;

R$_2$ is selected from the group consisting of alkyl, substituted alkyl, alkenyl, alkynyl, O-alkyl, cyclic group, polycyclic group, heterocyclic group,

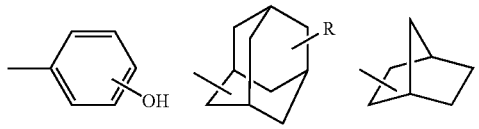

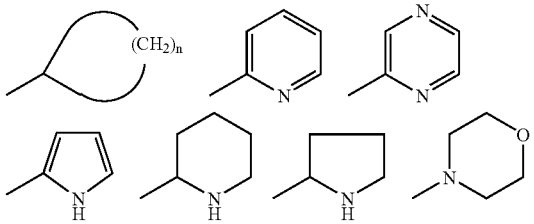

CH=CH$_2$, CH=C(CH$_3$)$_2$, C≡CH, CH$_2$OCH$_3$, CH(R)(CH$_2$)nCH$_2$Z and CH$_2$CH(R)(CH$_2$)nZ, R being selected from the group consisting of H, Z being selected from the group consisting of H, halogens, N$_3$, NCS, OH and OAc and n being selected from the group consisting of 0, 1 and 2; and R$_3$ is selected from the group consisting of alkyl, substituted alkyl, aryl, alkylaryl, O-alkyl, O-alkylaryl, cyclic group, heterocyclic group, n-C$_5$H$_{10}$Z', n-C$_6$H$_{12}$Z', n-C$_7$H$_{14}$Z' and 1',1'—C(CH$_3$)$_2$(CH$_2$)$_5$CH$_2$Z', Z' being selected from the group consisting of H, halogens, CN, N$_3$, NCS and OH;

with the proviso that:

when Y is C=O, X is NH, R$_1$ is H, R$_3$ is n-C$_5$H$_{10}$Z' and Z' is H, then R$_2$ cannot be selected from the group consisting of C$_{1-5}$ alkyl, CH$_2$CH$_2$OH, CH(CH$_3$)CH$_2$OH, (CH$_2$)$_m$OH (where m=1–10), CH(CH$_3$)CH$_2$F and CH$_2$CH$_2$OMe; and when Y is C=O, X is NH, R$_1$ is H, R$_3$ is selected from n-C$_6$H$_{12}$Z', n-C$_7$H$_{14}$Z' and 1'1'-C(CH$_3$)$_2$(CH$_2$)$_5$CH$_2$Z', Z' is H, then R$_2$ cannot be selected from the group consisting of C$_{1-5}$ alkyl and (CH$_2$)$_m$OH (where m=1–10).

11. The compound of claim 10 wherein R$_1$=H, R$_2$=CH(R)(CH$_2$)nCH$_2$Z, R=H and Z=OAc and n=0; and R$_3$=n-C$_5$H$_{10}$Z', Z'=H.

12. A medicinal preparation prepared from a compound comprising:

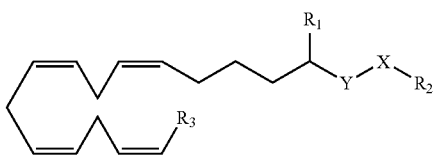

wherein X is one of the group consisting of C=O and NH and Y is the other of that group;

R$_1$ is selected from the group consisting of H and alkyl radicals;

R$_2$ is selected from the group consisting of alkyl, substituted alkyl, alkenyl, alkynyl, O-alkyl, cyclic group, polycyclic group and heterocyclic group; and R$_3$ is selected from the group consisting of alkyl, substituted alkyl, O-alkyl, aryl, alkylaryl, O-alkylaryl, cyclic and heterocyclic radicals;

with the proviso that:

when Y is C=O, X is NH, R$_1$ is H, R$_3$ is n-C$_5$H$_{10}$Z' and Z' is H, then R$_2$ cannot be selected from the group consisting of C$_{1-5}$ alkyl, CH$_2$CH$_2$OH, CH(CH$_3$)CH$_2$OH, (CH$_2$)$_m$OH (where m=1–10), CH(CH$_3$)CH$_2$F and CH$_2$CH$_2$OMe; and when Y is C=O, X is NH, R$_1$ is H, R$_3$ is selected from n-C$_6$H$_{12}$Z', n-C$_7$H$_{14}$Z', and 1'1'-C(CH$_3$)$_2$ (CH₂)₅CH₂Z', and Z' is H, then R₂ cannot be selected from the group consisting of $C_{1-5}$ alkyl and $(CH_2)_mOH$ (where m=1–10).

13. A medicinal preparation prepared from a compound comprising:

[Structure showing macrocycle with X-Y-R₂ and R₁, R₃ substituents]

wherein X is one of the group consisting of C=O and NH and Y is the other of that group;
R₁ is selected from the group consisting of H and alkyl radicals;
R₂ is selected from the group consisting of alkyl, substituted alkyl, alkenyl, alkynyl, O-alkyl, cycloalkyl, polycyclic and heterocyclic radicals; and
R₃ is selected from the group consisting of alkyl, substituted alkyl, O-alkyl, aryl, alkylaryl, O-alkylaryl, cyclic and heterocyclic radicals
with the proviso that:
when X is C=O, Y is NH, R₁ is H, R₃ is n-C₅H₁₀Z' and Z' is H, then R₂ can not be selected from the group consisting of $C_{1-5}$ alkyl, CH₂CH₂OH, CH(CH₃)CH₂OH, $(CH_2)_mOH$ (where m=1–10), CH(CH₃)CH₂F and CH₂CH₂OMe; and
when X is C=O, Y is NH, R₁ is H, R₃ is selected from n-C₆H₁₂Z', n-C₇H₁₄Z', and 1'1'-C(CH₃)₂(CH₂)₅CH₂Z' and Z' is H, then R₂ cannot be selected from the group consisting of $C_{1-5}$ alkyl and $(CH_2)_mOH$ (where m=1–10).

14. A compound of claim 1 wherein:
R₁ is selected from the group consisting of H, CH₃ and alkyl
R₂ is selected from the group consisting CH2CH=CH2, C≡CH, CH(R)CH₂Z, CH₂CH(R)Z and CH(R)(CH₂)nCH₂Z, R being selected from the group consisting of H, CH₃, CH₂CF₃ and (CH₃)₂, Z being selected from the group consisting of H, halogens, N₃, NCS and OH and n being selected from the group consisting of 0, 1 and 2; and
R₃ is selected from the group consisting of n-C₅H₁₀Z', n-C₆H₁₂Z', n-C₇H₁₄Z' and 1',1'—C(CH₃)₂(CH₂)₅CH₂Z', Z' being selected from the group consisting of H, halogens, CN, N₃, NCS and OH.

15. A compound of claim 1 selected from:

[Six structures showing AA-NH-C(=O) derivatives with various substituents: F with methyl, N₃ with methyl, allyl, F with stereochemistry, Cl ethyl, alkyne, I with methyl, Cl propyl]

-continued

[Structure: AA-C(=O)-NH-CH₂-CF₃]

16. A compound of claim 10 selected from:

[Three structures: AA-CH₂-NH-C(=O)-CH₂CH₂-OH, AA-CH₂-NH-C(=O)-CH₂-OAc, AA-CH₂-NH-C(=O)-CH₂-OH]

17. A medicinal preparation of claim 12, wherein:
R₁ is selected from the group consisting of H and CH₃;
R₂ is selected from the group consisting of

[Structures: p-hydroxyphenyl, adamantyl with R, norbornyl, cycloalkyl (CH₂)n, pyridyl, pyrazinyl, pyrrolyl, piperidyl, pyrrolidinyl, morpholinyl]

CH=CH₂, CH=C(CH₃)₂, C≡CH, CH₂OCH₃, CH(R)(CH₂)nCH₂Z and CH₂CH(R)(CH₂)nZ, R being selected from the group consisting of H and CH₃, Z being selected from the group consisting of H, halogens, N₃, NCS, OH and OAc and n being selected from the group consisting of 0, 1 and 2; and
R₃ is selected from the group consisting of n-C₅H₁₀Z', n-C₆H₁₂Z', n-C₇H₁₄Z' and 1',1'—C(CH₃)₂(CH₂)₅CH₂Z', Z' being selected from the group consisting of H, halogens, CN, N₃, NCS and OH.

18. A medicinal preparation of claim 15, wherein:
R₁ is selected from the group consisting of H and CH₃;
R₂ is selected from the group consisting of CH2CH=CH2, C—CH, CH(R)CH₂Z, CH₂CH(R)Z and CH(R)(CH₂)nCH₂Z, R being selected from the group consisting of H, CH₃, CH₂CF₃ and (CH₃)₂, Z being selected from the group consisting of H, halogens, N₃, NCS and OH and n being selected from the group consisting of 0, 1 and 2; and
R₃ is selected from the group consisting of n-C₅H₁₀Z', n-C₆H₁₂Z', n-C₇H₁₄Z' and 1',1'—C(CH₃)₂(CH₂)₅CH₂Z', Z' being selected from the group consisting of H, halogens, CN, N₃, NCS and OH.

19. The compound of claim 1 wherein $R_2$ is selected from the group consisting of
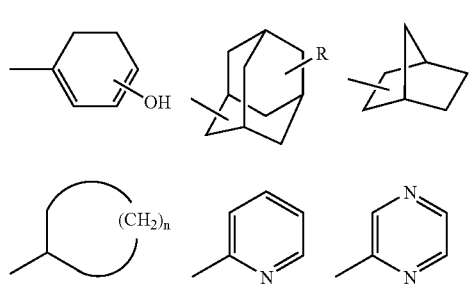
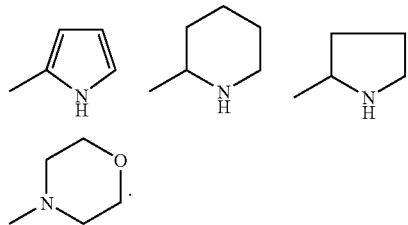

UNITED STATES PATENT AND TRADEMARK OFFICE
CERTIFICATE OF CORRECTION

| | |
|---|---|
| PATENT NO. | : 7,161,016 B1 |
| APPLICATION NO. | : 09/600786 |
| DATED | : January 9, 2007 |
| INVENTOR(S) | : Makriyannis et al. |

It is certified that error appears in the above-identified patent and that said Letters Patent is hereby corrected as shown below:

<u>Column 12</u>:

Line 15, after "H" insert --and $CH_3$--.

Line 30, after "C=O" delete "," and insert --and--.

Line 66, after "C=O" delete "," and insert --and--.

<u>Column 14</u>:

Line 53, delete "claim 15" and substitute --claim 13--.

Line 56, delete "C—CH" and insert --C≡CH--.

UNITED STATES PATENT AND TRADEMARK OFFICE
CERTIFICATE OF CORRECTION

PATENT NO. : 7,161,016 B1
APPLICATION NO. : 09/600786
DATED : January 9, 2007
INVENTOR(S) : Makriyannis et al.

It is certified that error appears in the above-identified patent and that said Letters Patent is hereby corrected as shown below:

Column 16:

Line 13, insert:

-- 20. A compound of claim 10, wherein:
$R_1$ is selected from the group consisting of H, $CH_3$ and alkyl;
$R_2$ is selected from the group consisting of

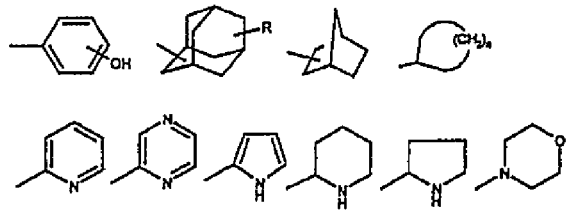

$CH=CH_2$, $CH=C(CH_3)_2$, $C\equiv CH$, $CH_2OCH_3$, $CH(R)(CH_2)nCH_2Z$ and $CH_2CH(R)(CH_2)nZ$, R being selected from the group consisting of H and $CH_3$, Z being selected from the group consisting of H, halogens, $N_3$, NCS, OH and OAc and n being selected from the group consisting of 0, 1 and 2; and
$R_3$ is selected from the group consisting of n-$C_5H_{10}Z'$, n-$C_6H_{12}Z'$, n-$C_7H_{14}Z'$ and 1',1'-$C(CH_3)_2(CH_2)_5CH_2Z'$, Z' being selected from the group consisting of H, halogens, CN, $N_3$, NCS and OH. --

Signed and Sealed this

Twenty-third Day of October, 2007

JON W. DUDAS
*Director of the United States Patent and Trademark Office*